US00PP25543P2

(12) United States Plant Patent
van Noort

(10) Patent No.: US PP25,543 P2
(45) Date of Patent: May 12, 2015

(54) ***GERANIUM* PLANT NAMED 'NOORTHAVA'**

(50) Latin Name: *Geranium wallichianum*
Varietal Denomination: Noorthava

(71) Applicant: Marco van Noort, Warmond (NL)

(72) Inventor: Marco van Noort, Warmond (NL)

(73) Assignee: Marco Van Noort Breeding, BV, Warmond (NL)

( * ) Notice: Subject to any disclaimer, the term of this patent is extended or adjusted under 35 U.S.C. 154(b) by 127 days.

(21) Appl. No.: 13/815,732

(22) Filed: Mar. 15, 2013

(51) Int. Cl.
*A01H 5/00* (2006.01)

(52) U.S. Cl.
USPC ..... Plt./324

(58) Field of Classification Search
USPC ..... Plt./324
See application file for complete search history.

(56) References Cited

PUBLICATIONS

PLUTO Plant Variety Database Sep. 16, 2014. p. 1.*

* cited by examiner

*Primary Examiner* — Annette Para
(74) *Attorney, Agent, or Firm* — Penny J. Aguirre

(57) ABSTRACT

A new cultivar of *Geranium wallichianum*, 'Noorthava', characterized by its large flowers that are light blue-violet in color with dark purple veins, its long blooming season, and its strong and healthy growth habit.

2 Drawing Sheets

Botanical classification: *Geranium wallichianum.*
Cultivar designation: 'Noorthava'.

BACKGROUND OF THE INVENTION

The present invention relates to a new and distinct cultivar of *Geranium* plant, botanically known as *Geranium wallichianum* 'Noorthava' and will be referred to hereafter by its cultivar name, 'Noorthava'. 'Noorthava' is a new cultivar of herbaceous perennial grown for use as a garden plant.

'Noorthava' originated as a seedling that arose in the Inventor's trial plot from seed planted from open pollination of unnamed plants of *Geranium wallichianum* from the Inventor's breeding line in Warmond, The Netherlands in 2007. The specific parents are unknown. The new *Geranium* was selected as a single unique plant in July of 2008.

Asexual propagation of the new cultivar was first accomplished by division in Warmond, The Netherlands in 2010 by the inventor. Asexual propagation by division and tissue culture has determined that the characteristics of the new cultivar are stable and are reproduced true to type in successive generations.

SUMMARY OF THE INVENTION

The following traits have been repeatedly observed and represent the characteristics of 'Noorthava'. These attributes in combination distinguish 'Noorthava' as a new and distinct cultivar of *Geranium.*

1. 'Noorthava' exhibits large flowers (larger than is typical for cultivars of *Geranium wallichianum*)
2. 'Noorthava' exhibits light blue-violet flowers with dark purple veins.
3. 'Noorthava' exhibits a long blooming season; blooming for about 8 weeks in The Netherlands.
4. 'Noorthava' exhibits a strong growth habit with healthy foliage.

'Noorthava' differs from the proprietary plants that are prossible parents in that it have larger flowers with more conspicuous veining. 'Noorthava' can be most closely compared to the cultivars 'Jolly Bee' (U.S. Plant Pat. No. 12,148), 'Buxton's Variety' (not patented) and 'Pink Penny' (U.S. Plant Pat. No. 12,148). 'Jolly Bee' differs from 'Noorthava' in having smaller flowers and in having more purple coloration in the flowers. 'Buxton's Variety' differs from 'Noorthava' in having smaller flowers. 'Pink Penny' differs from 'Noorthava' in having pink flowers and in being wider in spread.

BRIEF DESCRIPTION OF THE DRAWING

The accompanying colored photographs illustrate the overall appearance and distinct characteristics of the new *Geranium*. The photographs were taken of one year-old plants of 'Noorthava' as grown outdoors in a nursery bed in Warmond, The Netherlands.

The photograph in FIG. 1 is a view of multiple plants of 'Noorthava' planted in the nursery bed.

Figure 1:
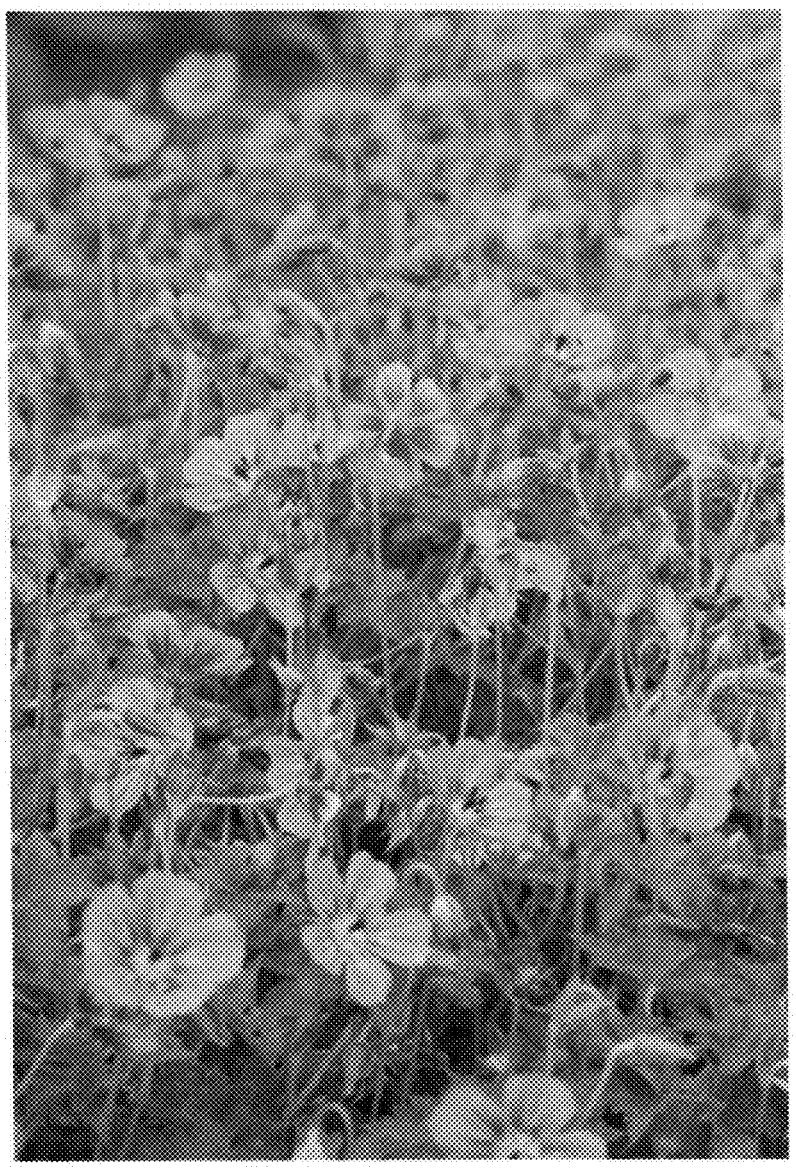
Figure 2:
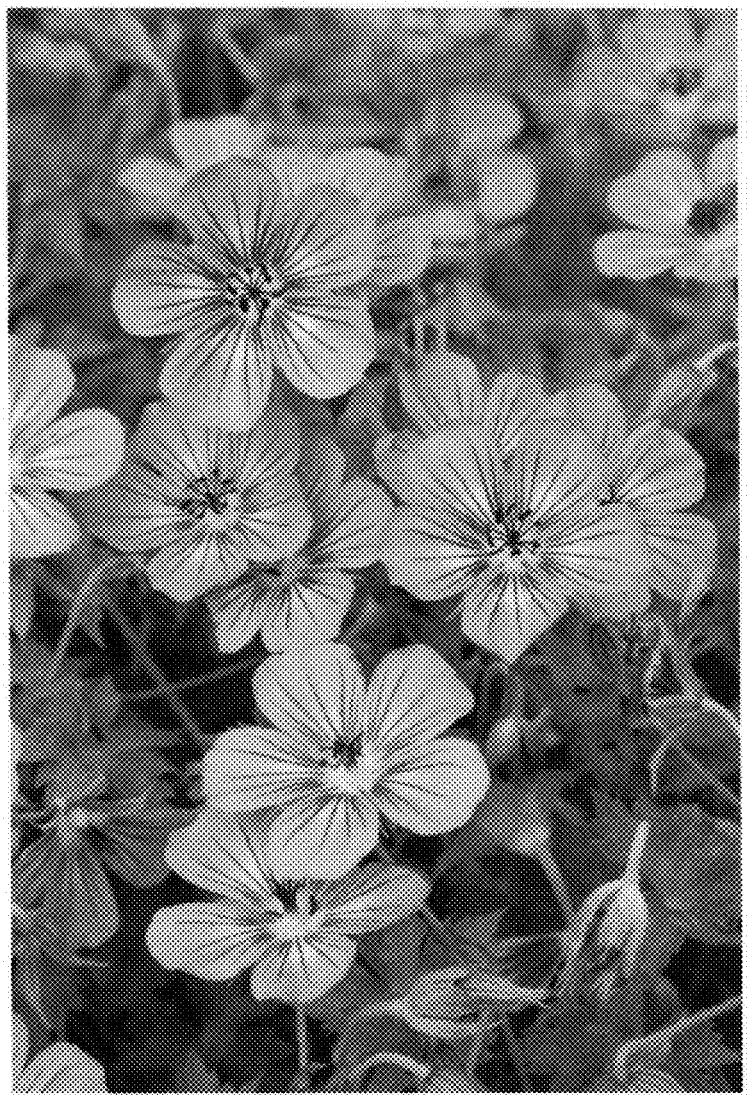

The photograph in FIG. 2 provides a close-up view of the flowers of 'Noorthava'.

The colors in the photographs are as close as possible with the digital photography and printing techniques utilized and the color codes in the detailed botanical description accurately describe the colors of the new *Geranium.*

DETAILED BOTANICAL DESCRIPTION OF THE PLANT

The following is a detailed description of one year-old plants of the new cultivar as grown outdoors in a nursery bed in Warmond, The Netherlands. Plants were grown under average day temperatures of 14° C. to 30° C. and average night temperatures of 6° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—About 8 weeks in mid summer in The Netherlands.

*Plant type*.—Herbaceous perennial.

*Plant habit*.—Mounded with upright flowers, moderately spreading.

*Height and spread*.—Reaches about 20 cm in height and 30 cm in spread.

*Cold hardiness*.—At least to U.S.D.A. Zone 5.

*Heat tolerance*.—At least tolerant to temperature up to 35° C.

*Diseases and pests*.—No paticular susceptibility or resistance to diseases or pests has been observed, however plants has been observed to be healthy under the conditions grown.

*Root description*.—Fibrous roots extending from stout rootstock.

*Growth rate*.—Moderately vigorous.

*Growth habit*.—Strong.

*Propagation*.—Division and In vitro propagation.

Stem description:

*Stem size*.—Average of 10.7 cm in length and 2.5 mm in width.

*Stem shape*.—Round.

*Stem strength*.—Moderately strong.

*Stem color*.—172B to 175B upper surface, and 144C under surface.

*Stem surface*.—Moderately glossy and moderately covered with dense short soft hairs, average of 0.7 mm in length and 156D in color.

*Internode length*.—Average of 4.5 cm.

*Branching habit*.—Moderately branched, about 4 lateral branches, average of 10.1 cm in length and 2.5 mm in width on a 1 year-old plant.

Foliage description:

*Leaf shape*.—Orbicular (overall shape), palmately cleft with an average of five lobes.

*Leaf division*.—Simple.

*Leaf base*.—Hastate (not overlapping).

*Leaf apex*.—Acute.

*Leaf venation*.—Palmate, upper surface; 146B to 146C in color, lower surface; 144B to 144C in color.

*Leaf margins*.—Palmately cleft into an average of five lobes, margins of lobes serrate.

*Leaf attachment*.—Petiolate.

*Leaf arrangement*.—Opposite.

*Leaf surface*.—Upper and lower surfaces dull, upper surface moderately covered with dense very short hairs, average length 0.5 mm in length and between N155A and 157D in color, lower surface main and secondary veins densely covered with short hairs an average of 1 mm in length and between N155A and 157D in color.

*Leaf color*.—Young upper surface; 143A, young lower surface; 144A, mature upper surface; N137A to N137B, mature lower surface; 138C.

*Leaf size*.—Average of 4.5 cm in length and 5.3 cm in width.

*Leaf quantity*.—Average of 4 (2 pairs) per lateral branch.

*Petioles*.—Average of 5.8 cm in length and 15 mm in width, color 175C to 175D on upper surface and 145A on lower surface, surface pubescent with coarse hairs.

*Stipules*.—Present at the base of the basal leaves, ovate in shape, average of 1.3 cm in length and 1.1 cm in width, both surfaces 145B in color, base becomes lighter; 145D.

Flower description:

*Inflorescence type*.—Single, rotate, arranged in pairs.

*Lastingness of flowers*.—About 7 days, self cleaning.

*Flower size*.—Average of 1 cm in height and 4.1 cm in diameter.

*Flower fragrance*.—None.

*Flower number*.—Average of 1 flower per lateral stem.

*Flower aspect*.—Upright to slightly outward.

*Flower bud size*.—An average of 1.3 cm in length, up to 6 mm in width.

*Flower bud color*.—144A to 144B, veins and base N186C, buds covered in short hairs 1 mm in length and N155A in color.

*Flower bud shape*.—Ovate.

*Corolla features*.—Petals are unfused and arranged in a rotate form.

*Petal number*.—5.

*Petal shape*.—Obcordate.

*Petal color*.—When opening upper surface; between 90D and 92A, base 85D, veins N79A to N79B, when opening lower surface; N87D, base and veins N79C, when fully open upper surface; between 90D and 92A, base 85D, veins N79A to N79B, when fully open lower surface; N87D, base and veins N79C, petal color fading to; N81B, base 76C to 76D, veins N79C to N79D.

*Petal surface*.—Smooth, velvety and slightly glossy and densely covered with pubescence at the base; average length of 0.8 mm in length and N155A in color (upper and lower surface).

*Petal margins*.—Entire.

*Petal apex*.—Straight, obtuse to slightly retuse.

*Petal size*.—Average of 2.1 cm in length and 1.7 cm in width.

*Calyx form*.—Rotate, slightly cupped.

*Calyx size*.—Average of 7 mm in length and 2.2 cm in width.

*Sepal number*.—Average of 5.

*Sepal shape*.—Oblong to elliptic.

*Sepal margin*.—Entire.

*Sepal size*.—Average of 1.5 mm length, 4.5 mm in width.

*Sepal surface*.—Upper and lower surface dull.

*Sepal apex*.—Mucronate.

*Sepal base*.—Cuneate.

*Sepal color*.—Immature upper and lower surface; 144A to 144B, veins and base N186C, mature upper and lower surface; 144A, veins and base 183B to 183C.

*Peduncle*.—Average of 7.7 cm in length and 1.5 mm in diameter, moderate to strong, held at about a 67° angle relative to lateral branch, color 144A to 144B, pubescent surface.

*Pedicel*.—Round in shape, an average of 3.9 cm in length and 1 mm in width, moderately strong, lateral flowers are held at an average of 15° to peduncle, color 144C to 144D, pubescent surface.

Reproductive organs:

*Gynoecium.*—1 pistil, about 1.1 cm in length, 5 stigmas are decurrent and N186C in color, style is about 7 mm in length and 145A in color, ovary is 145B to 145C in color.

*Androcoecium.*—10 stamens, anthers are dorsifixed, oblong in shape, 3 mm in length, and N186B in color, filament is 7 mm in length and 187C in color with base 145D, pollen is low in abundance and 198C to 198D in color.

*Fruit/seeds.*—No fruit or seeds detected to date.

It is claimed:

1. A new and distinct cultivar of *Geranium* plant named 'Noorthava' as herein illustrated and described.

* * * * *